(12) United States Patent
Swider et al.

(10) Patent No.: US 7,040,529 B2
(45) Date of Patent: May 9, 2006

(54) DROP BOX FOR ISOLATING RECEIVED ITEMS

(75) Inventors: John T. Swider, Port Crane, NY (US); Patrick J. Fitzgibbons, Newark Valley, NY (US)

(73) Assignee: Lockheed Martin Corporation, Bethesda, MD (US)

( * ) Notice: Subject to any disclaimer, the term of this patent is extended or adjusted under 35 U.S.C. 154(b) by 0 days.

(21) Appl. No.: 10/395,920

(22) Filed: Mar. 24, 2003

(65) Prior Publication Data

US 2003/0226884 A1    Dec. 11, 2003

Related U.S. Application Data

(63) Continuation-in-part of application No. 10/309,541, filed on Dec. 4, 2002.

(60) Provisional application No. 60/337,134, filed on Dec. 4, 2001, provisional application No. 60/339,899, filed on Dec. 10, 2001, provisional application No. 60/367,169, filed on Mar. 25, 2002.

(51) Int. Cl.
*B65G 11/04* (2006.01)

(52) U.S. Cl. .............................. 232/45; 232/30; 232/31; 232/43.2

(58) Field of Classification Search .................. 232/45, 232/44, 30–32, 43.2; 193/8; 220/908, 908.3; 312/1
See application file for complete search history.

(56) References Cited

U.S. PATENT DOCUMENTS

| 329,688 A | 11/1885 | Taylor |
| 402,855 A | 5/1889 | Paulsen |
| 726,821 A | 4/1903 | Lambert |
| 948,815 A | 2/1910 | Ehrlich |
| 1,256,044 A * | 2/1918 | Schilling .................... 232/31 |
| 1,338,400 A | 4/1920 | Sachs |
| 1,424,519 A * | 8/1922 | Richardson ................. 40/306 |
| 1,424,520 A * | 8/1922 | Richardson et al. ..... 220/254.2 |
| 1,451,343 A * | 4/1923 | Panagopolous ............. 232/30 |
| 2,125,122 A * | 7/1938 | Mongiello .................. 220/825 |
| 2,421,221 A * | 5/1947 | Rothe .......................... 232/30 |
| 2,531,444 A * | 11/1950 | Lane .......................... 312/211 |

(Continued)

FOREIGN PATENT DOCUMENTS

DE    136666    12/1902

(Continued)

OTHER PUBLICATIONS

International Search Report, Nov. 20, 2003, PCT/US02/34514 (12078-198PCT).

(Continued)

*Primary Examiner*—William L. Miller
(74) *Attorney, Agent, or Firm*—Perkins Smith & Cohen LLP; Peter J. Borghetti; Harvey Kaye

(57) ABSTRACT

A mail drop box for isolating mail deposited therein having a closable, removable container inside the box for receiving mail and has an opening in the top. A plurality of mail transmitting chutes each having a deposit port at its upper end and an exit port at its lower end to receive mail through the deposit port and direct such mail into the container. The opening in the removable container is closed when desired to isolate mail from the ambient atmosphere and permit removal of the container without exposing the ambient atmosphere to hazardous particles which may be on or in such mail. A removal door permits removal of the container. A transparent door is adjacent to, but inside of, the removal door for allowing viewing of the opening of the container when the removal door is open.

18 Claims, 13 Drawing Sheets

U.S. PATENT DOCUMENTS

| | | | |
|---|---|---|---|
| 3,793,756 A * | 2/1974 | Kay et al | 40/306 |
| 3,866,824 A * | 2/1975 | Lewis | 232/43.2 |
| 3,981,436 A | 9/1976 | Neal | |
| 3,982,690 A | 9/1976 | Krizan et al. | |
| 4,126,241 A * | 11/1978 | Klosk | 232/43.2 |
| 4,176,610 A | 12/1979 | Gansauge et al. | |
| 4,281,814 A | 8/1981 | Verwey | |
| 4,363,438 A | 12/1982 | Connor | |
| 4,573,416 A | 3/1986 | Masachika | |
| 4,593,816 A | 6/1986 | Langenbeck | |
| 4,715,498 A | 12/1987 | Hanifl | |
| 5,007,581 A * | 4/1991 | Douglas | 232/43.2 |
| 5,050,743 A | 9/1991 | Lazzarotti | |
| 5,137,212 A | 8/1992 | Fiterman et al. | |
| 5,316,733 A | 5/1994 | Rune et al. | |
| 5,400,960 A | 3/1995 | Jeffs | |
| 5,470,546 A | 11/1995 | Hall | |
| 5,531,346 A | 7/1996 | Mosior | |
| 5,806,759 A * | 9/1998 | Axisa | 232/44 |
| 5,979,751 A | 11/1999 | Maddox | |
| 6,202,849 B1 | 3/2001 | Graham | |
| 6,299,061 B1 | 10/2001 | Henson | |
| 6,592,026 B1 | 7/2003 | Vilardi | 232/17 |
| 6,742,703 B1 | 6/2004 | Esakov et al. | |
| 2002/0124664 A1 | 9/2002 | Call et al. | |
| 2003/0106929 A1 | 6/2003 | Day et al. | 232/30 |
| 2003/0127505 A1 * | 7/2003 | Avant | 232/30 |
| 2003/0152480 A1 | 8/2003 | Sham | |
| 2003/0167740 A1 | 9/2003 | Murphy | |
| 2003/0222132 A1 | 12/2003 | Esakov et al. | |

FOREIGN PATENT DOCUMENTS

| | | |
|---|---|---|
| DE | 1982064 | 3/1968 |
| DE | 1759533 | 1/1970 |
| DE | 1956059 | 5/1970 |
| GB | 2310422 | 8/1997 |

OTHER PUBLICATIONS

WO 03/078957, Published PCT International Application, Publication Date Sep. 25, 2003, PCT/US02/34514 (12078-198PCT).

U.S. Postal Service, "Emergency Preparedness Plan for Protecting Postal Employees and Postal Customers from Exposure to Biohazardous Material . . . " Mar. 6, 2002 (including Appendices A-H).

* cited by examiner

DROP BOX FOR ISOLATING RECEIVED ITEMS

CROSS REFERENCE TO RELATED APPLICATIONS

The present application is a continuation-in-part application of U.S. patent application Ser. No. 10/309,541, filed Dec. 4, 2002 and entitled PUBLIC DROP BOX FOR ISOLATING RECEIVED ITEMS, which claims the benefit of U.S. Provisional Application Ser. No. 60/337,134, filed Dec. 4, 2001 and entitled COLLECTION BOX, and also claims benefit of U.S. Provisional Application Ser. No. 60/339,899, filed Dec. 10, 2001 and entitled SECURE COLLECTION BOX, and also claims benefit of U.S. Provisional Application Ser. No. 60/367,169 filed Mar. 25, 2002 entitled COLLECTION BOX WITH SEALABLE HAMPER. The above-identified applications are incorporated herein by reference.

FIELD OF THE INVENTION

The present invention generally relates to depository boxes, such as mailboxes, and, in particular, to such mailboxes which isolate items received therein to prevent the spread of contaminants.

BACKGROUND OF THE INVENTION

The recent incidents of anthrax-laced letters being transported through the United States Postal Service (USPS) facilities by unsuspecting mail handlers to unsuspecting recipients has alarmed the nation and the world. Currently, the tainted letters are discovered after the recipient accepts delivery or by alert postal employees noticing white powder that could be anthrax on mail parcels, sorting and distribution equipment, or themselves. There appear to be no current security devices or procedures that are available to intercept such letters at the earliest source of introduction into the USPS system.

Therefore, it would be advantageous to be able to isolate items dropped into mailboxes and other public drop boxes, so that adequate testing may be performed to detect the presence of any contaminants.

Terrorist activities in the United States have caused an urgent need for a means of protecting the public and the US Postal Service mail carriers from contaminates placed into the mail collection stream. The recent incidents of anthrax laced letters being transported through the United States Postal Service (USPS) facilities to unsuspecting recipients has alarmed the nation and the world. Currently, the tainted letters are discovered after the recipient accepts delivery or by alert postal employees noticing white powder that could be anthrax on mail parcels, sorting and distribution equipment, or themselves.

In particular, one style of collection box used by the US Postal Service is called the jumbo box, which includes a portable hamper option and which has a plurality of drop slots for receiving mail. The jumbo box is used in areas where customers deposit high volumes of mail pieces. The mail pieces are collected in the hamper and transported in bulk to the processing facility. There appears to be no current security devices or procedures that are available to isolate such letters within the hamper of a jumbo box, as well as the interior of the jumbo box.

Co-pending, commonly owned, patent application, Ser. No. 10/315,329, filed Dec. 10, 2002, to R. Felice, discloses a closeable mail receptacle for use inside of a drop box, which includes a rectangular tub having an open top, and a top cover adapted to engage the open top and close the tub either prior to or during removal of the tub from the drop box.

Co-pending, commonly owned, provisional application, Ser. No. 60/400,466, filed Aug. 2, 2002, to J. Swider et al., discloses a system and method which incorporates the use of sack supporting means and a contaminated air evacuation system for the collection of mail deposited in mail collection boxes providing protection against inadvertent release of any contaminants contained within such deposited mail.

Several U.S. patents disclose hamper lids or covers that are pivotally and/or removably attached to a hamper. U.S. Pat. No. 3,958,715, issued May 25, 1976, to J. Capelli; U.S. Pat. No. 3,982,690, issued Sep. 28, 1976 to B. Krizan et al; U.S. Pat. No. 4,057,309, issued Nov. 8, 1977, to E. Fragale; U.S. Pat. No. 4,180,113, issued Dec. 25, 1979, to J. Liebling; U.S. Pat. No. 4,218,103, issued 19, 1980; U.S. Pat. No. 4,246,945, issued Jan. 27, 1981, to N. Sterling; U.S. Pat. No. 4,281,814, issued Aug. 4, 1981, to R. Verwey; U.S. Pat. No. 4,354,543, issued Oct. 19, 1982; U.S. Pat. No. 4,585,283, issued Apr. 29, 1986.

Several U.S. patents disclose other uses for hampers in mail collection and process applications in conjunction with mail chutes. U.S. Pat. No. 4,363,438, issued Dec. 14, 1982, to C. Connor, discloses a mailbox having a slidable mailbag holding frame attached therein to position a mailbag below a mail chute to receive deposited mail articles and to slide the mailbag out of the mailbox for removal of the mailbag for mail processing. U.S. Pat. No. 4,690,283, issued Sep. 1, 1987, to R. Carrell, discloses a mail processing apparatus having mail hampers removably attached to portable frames positioned below mail chutes. U.S. Pat. No. 5,050,743, issued Sep. 24, 1991, to S. Lazzarotti, discloses mail sacks removably attachable to stationary frames disposed below mail chutes.

SUMMARY OF THE INVENTION

Accordingly, one embodiment of the present invention provides a publicly accessible drop box adapted for isolating items deposited therein, comprising a securable enclosure, a deposit port forming part of the securable enclosure and adapted to allow items to be dropped therethrough into the securable enclosure, a closeable container having an opening and located within the securable enclosure for receiving items, and a closure device adapted for closing the opening prior to removal of the container from the securable enclosure.

The deposit port may include a housing forming a reception chamber adapted for receiving items deposited into the mail box, which housing includes an entrance and is adapted to allow opening of the entrance for receiving deposited items in the reception chamber. The depository port may also include a drop box opening formed as part of the securable enclosure, wherein the housing is rotatably mounted within the drop box for causing exposure of the entrance through the drop box opening by rotational alignment with the drop box opening and for causing closure of the entrance by rotational misalignment with the drop box opening.

The drop box may include a view port located in the securable enclosure and adapted to allow viewing of the opening of the closeable container within the securable enclosure. This view port may be a transparent panel located in a side of the drop box, and be covered by a securable door.

The drop box may include a manipulation device extending into the securable enclosure and adapted to enable manipulation of the closure device or to enable movement of any items in proximity to the opening of the container, by a user located outside the securable enclosure without exposing the user to any items located within the securable enclosure. This manipulation device may be a hazardous material mitt or glove extending into the drop box and having an open end for manual insertion, which open end is sealed to a side of the securable enclosure to isolate a user of the mitt or glove from items within the drop box. The open end of the hazardous material mitt or glove may be sealed to a transparent panel in a side of the drop box, which panel forms a view port into the securable enclosure.

The closeable container may be a standard size mail flat tray having a rectangular open top and a top cover adapted for engaging the rectangular open top and preventing air from escaping from the container. The closure device may include a door hinged to the top cover and adapted to be left open for receiving articles, and further adapted for closure prior to removal of the container from the securable enclosure.

The drop box may include a duct forming a channel for directing items from the depository port to the opening of the container, and a shutter mounted to the securable enclosure and adapted for closing the channel. This duct and a side of the securable enclosure may form a chamber adapted for storing the shutter in an open position. The shutter may be adapted for removable coupling to the container to provide closure of the shutter with the removal of the container from the securable enclosure.

The closure device of the drop box may be adapted to close the opening of the container during removal of the container from the securable enclosure. A cover may be included and adapted to engage and close the container during removal of the container from the securable enclosure. The drop box may further include a pair of opposed horizontal rails adapted for engaging the container within the securable enclosure and further adapted to engage the cover during removal of the container from the securable enclosure. The drop box may further include second and third securable doors located in opposing sides of the drop box and oriented generally orthogonally to the horizontal rails, wherein the horizontal rails and the second and third doors are adapted to allow simultaneous insertion of one closeable container into the drop box and removal of another closeable container.

In another embodiment, the present invention provides a deposit port structure for a mail box, including a housing forming a reception chamber adapted for receiving items deposited into the mail box, which housing includes an entrance and is adapted to allow opening of the entrance for receiving deposited items in the reception chamber. The deposit port may also include a drop box opening formed as part of the securable enclosure, wherein the housing is rotatably mounted within the drop box for causing exposure of the entrance through the mail box opening by rotational alignment with the mail box opening and for causing closure of the entrance by rotational misalignment with the mail box opening.

The housing may include an exit from the chamber, and may further be adapted to open the exit by rotation of the housing after the closure of the entrance. The deposit port structure may further include a closure surface affixed to the mailbox in a position to block the exit while the entrance is exposed through the mailbox opening. The housing may be rotatable in a first direction to a first position of alignment between the entrance and the mailbox opening and further rotatable in a second direction to a second position wherein the exit is open. This housing may be balanced to rest in the second position. The reception chamber entrance may be directed generally upwardly from the reception chamber and the exit may be directed generally downwardly from the reception chamber to enable gravitational movement of items through said chamber.

The housing may include a flange extending away from the reception chamber entrance in both directions of rotation of the housing, and this flange may be adapted to isolate a user of the drop box from items that have previously passed through the depository port.

One exemplary embodiment is a collection box being adapted with a mail chute, a sealable hamper, and an interior access door and an exterior sealed access door. Mail articles are deposited into a mail slot that guides the mail article into the mail chute and into the awaiting sealable hamper.

One embodiment of the sealable hamper includes a conventional hamper, wheels, lid with a hole, sliding door and sliding door mechanism. Alternatively, an impervious liner, made of a rigid molded structure or a flexible bag made of polymers, can be disposed within the hamper for increased contamination collection. The lid can be made of plywood, plastic, metal or any suitable material. The perimeter of the lid is fitted with a form skirt to seal the rim of the sealable hamper. The weight of the lid and the skirt assure the lid conforms to the possible unevenness of the wire frame rim.

Further, the lid includes a hole, preferably near its center portion, for the mail articles to enter the sealable hamper. The hole is covered by a door when the hamper is transported to a distribution center. Such a door may be in slidable contact with respect to the lid by a sliding door mechanism. One embodiment of the sliding door mechanism includes two opposing tracks disposed on either side of the hole and preferably of length greater that the hole. The door can be in frictional contact with the tracks and lid, thereby creating a seal with little or no air leakage from the interior of the hamper to the outside environment. Alternatively, sealing material, such as foam, can be adapted to the lid and/or tracks such that the door will be in slidable contact with the foam and the interior of the hamper will be isolated from the outside atmosphere.

The collection box includes two access doors. The exterior access door is similar to conventional collection box access doors with an improved seal to create a substantially air tight seal. The interior access door is transparent such that the sealable hamper and the slidable door are visible. The interior access door includes an access port sized for insertion of a tool or hand to open and close the slidable door. The tool is sufficiently long to enter the interior of the collection box is actuate the door open and closed. One potential storage location for the tool is on hooks or the like on the interior side of the exterior access door.

In operation, the mail carrier unlocks the exterior access door of the collection box and views the interior for mail overflow or jams. The carrier removes the tool from its storage place, inserts the tool into the port, and slides the door closed. The carrier unlocks the interior access door and slides the sealed hamper out of the collection box for transportation. A replacement hamper pre-fitted with a lid is pushed in and located inside the collection box. The carrier opens the sliding door with the tool allowing for acceptance of mail articles. The carrier closes and locks the access doors and transports the removed hamper to a distribution facility.

For a better understanding of the present invention, together with other and further objects thereof, reference is made to the accompanying drawings and detailed description.

BRIEF DESCRIPTION OF THE DRAWINGS

The present invention is illustratively shown and described in reference to the accompanying drawings, in which.

DETAILED DESCRIPTION OF THE DRAWINGS

Figure 1:
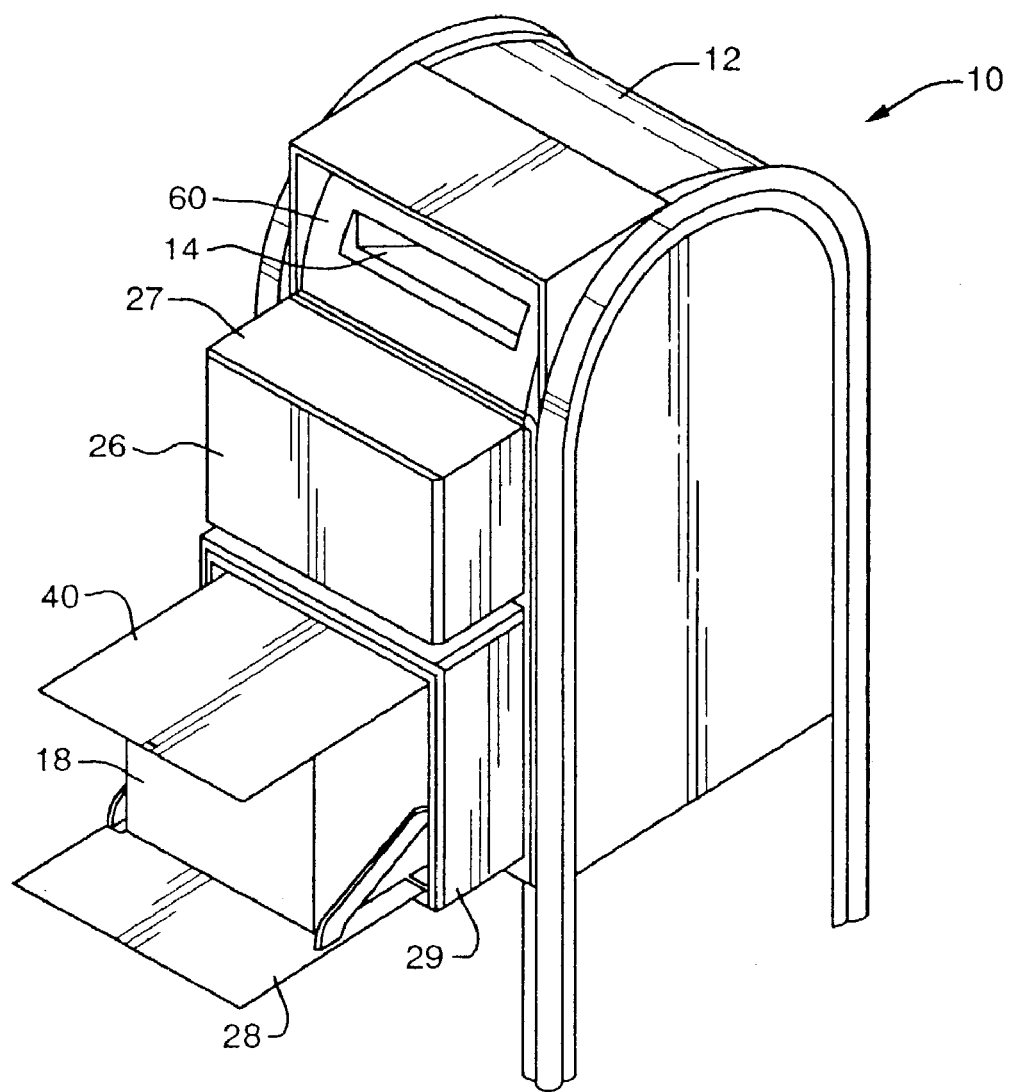
FIG. 1 is a perspective view of a drop box constructed in accordance with one embodiment of the present invention.
Figure 2:
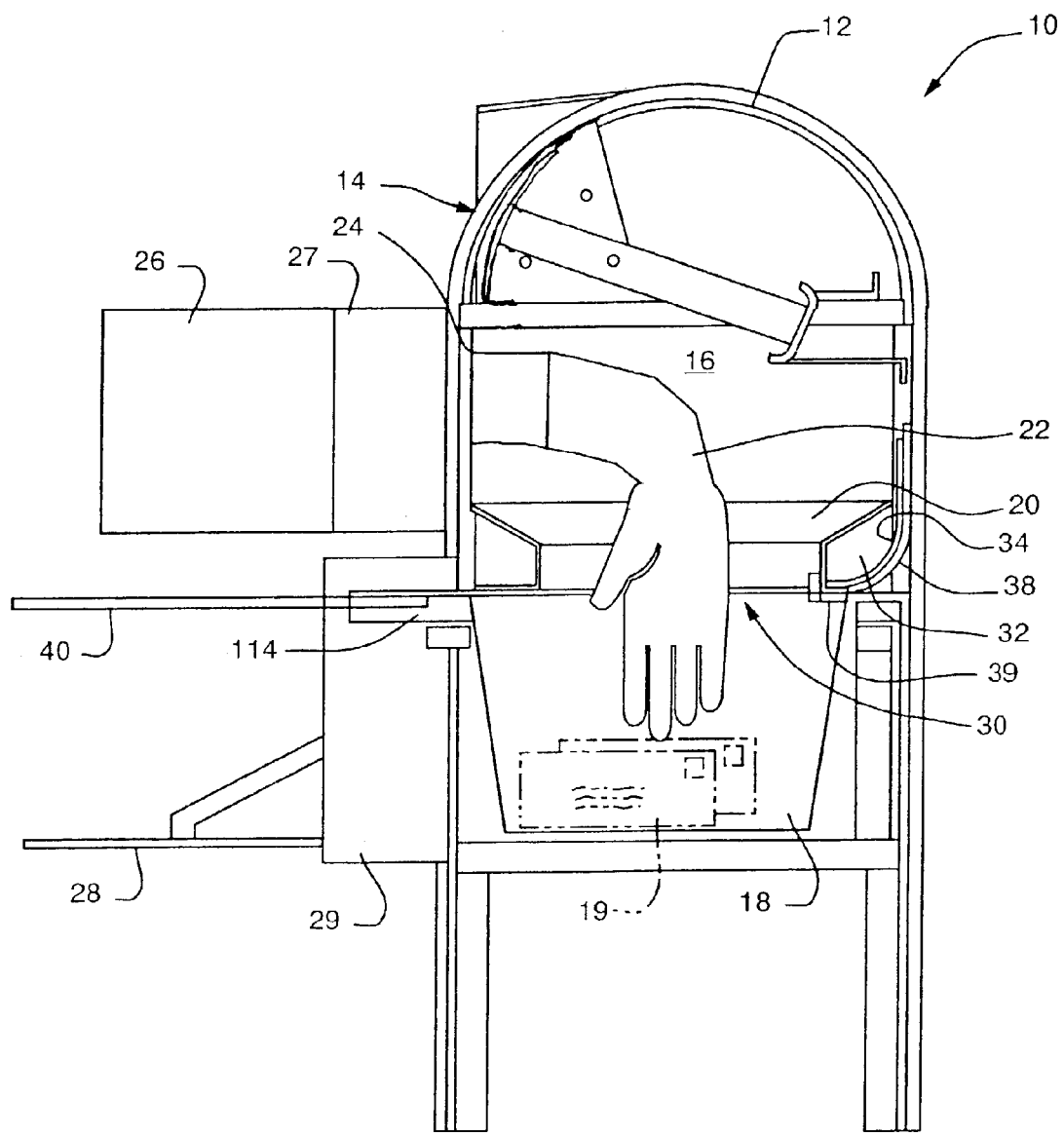
FIG. 2 is a side view diagram of the inside of the public drop box of FIG. 1.

FIGS. 1 and 2 are perspective and diagrammatic views, respectively, of a mail box 10 constructed in accordance with one embodiment of the present invention for isolating items deposited therein. Mail box 10 generally includes a securable enclosure 12 having a deposit port 14 and forming a central chamber 16 in which is located a closeable container 18 for receiving deposited mail articles 19. Mailbox 10 also includes a duct 20, which forms a channel for directing deposited mail articles into container 18.

A manipulation device 22 is shown extending into securable enclosure 12, in the form of a hazardous material glove or mitt. Manipulation device 22 is mounted to a side 24 of mailbox 10 and access thereto is controlled by a securable door 26. Securable door 26 is shown hinged to an additional housing 27, which may be used for the storage of manipulation device 22 while mail box 10 is available for public deposits of mail articles. Housing 27 may be retrofitted to a standard mailbox.

Another securable door 28 is used to allow for the removal and replacement of container 18. Securable door 28 opens downwardly to provide support for container 18 upon removal from mail box 10. Door 28 is affixed to an additional housing 29 for the purpose of retrofitting to standard mailboxes.

Duct 20 defines an opening 30 to container 18 for the purpose of directing deposited mail articles into container 18. Duct 20, in combination with mailbox 10, forms a chamber 32 for enclosing a shutter 34 used for closure of the opening 30. The movement of shutter 34 within chamber 32 is directed by an arcuate guide 38. Shutter 34 may also be removably attached to container 18 by a coupling 39 to cause opening and closure by the insertion and removal of container 18, respectively. Shutter 34 may also be opened and closed by a linkage connected to door 28. Manipulation device 22 may be used to open and close shutter 34. Manipulation device 22 also allows mail articles, that are piled up in container 18, to be cleared from opening 30 so that container 18 may be closed prior to or during its removal from mail box 10.

A separate cover 40 is also shown for engaging container 18 as it is removed from mailbox 10. Cover 40 is removed while container 18 is located within mailbox 10 and engages container 18 as container 18 is removed from mailbox 10.

In operation, mailbox 10 becomes a drop box adapted for isolating items deposited therein. Mailbox 10 forms a securable enclosure 12 having deposit port 14 adapted to allow items to be dropped through deposit port 14 into securable enclosure 12. Closeable container 18 is located within mailbox 10 for receiving deposited mail articles 19. Container 18 has a closeable opening in the form of shutter 34 or cover 40, and a closure device is provided for closing this opening prior to or during removal of container 18 from mail box 10.

Mail box 10 may further include duct 20 forming a channel for directing items from deposit port 14 to the opening of container 18, which opening 30 may thereby be defined by duct 20. Shutter 34 therefore provides one form of closure device for closing the opening 30. Duct 20 and the side of mailbox 10 may form a chamber for storing shutter 34 in an open position.

Mail box 10 may further include manipulation device 22 extending into the enclosure 12 and being adapted to enable manipulation of the closure device by a user located outside of mail box 10 or to enable movement of any deposited items in proximity to the opening 30 of container 18 and thereby facilitate closure of the opening.

Figure 3:
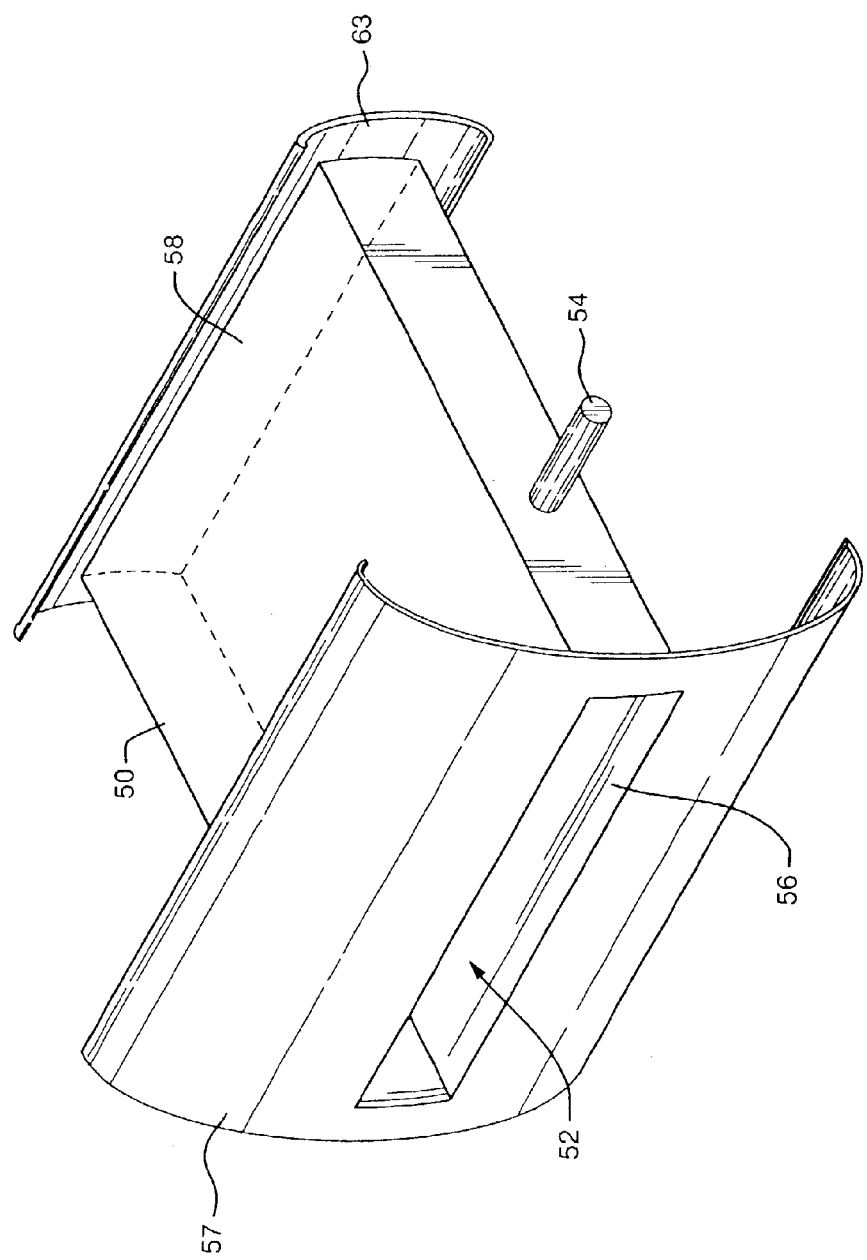
FIG. 3 is a perspective view of a portion of the drop box of FIGS. 1 and 2.
Figure 4:
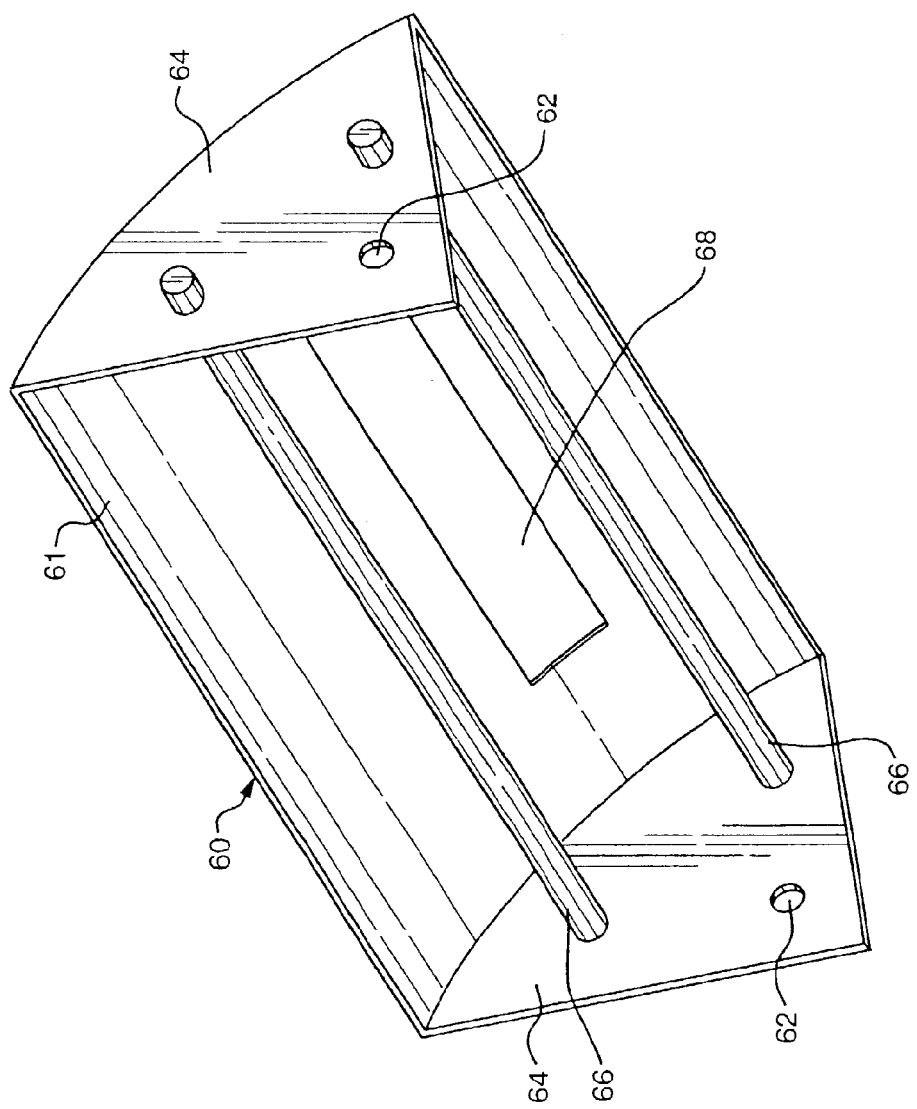
FIG. 4 is a perspective view of another portion of the drop box of FIGS. 1 and 2.

Deposit port 14 is shown in greater detail in FIGS. 3 and 4. Deposit port 14 primarily includes a housing 50 forming a chamber 52, which is adapted for rotation about an axis or axel 54. Chamber 52 generally includes an entrance 56 and an exit 58 (shown in phantom). Housing 50 also includes a partial shield or flange 57 extending in opposite directions of rotation for housing 50 from each side of entrance 56.

FIG. 4 shows a shield 60 which may be retrofitted to a common mail box by suitably affixing shield 60 over the typical opening used at the top of mail boxes, as shown in FIG. 1. Shield 60 provides a means for rotatably mounting housing 50 at openings 62. Shield 60 generally includes an arcuate member 61, which is affixed to and bounded by a pair of end plates 64. End plates 64 are generally normal to the axis of rotation of housing 50. Shield 60 further includes a pair of stabilizing rods 66 mounted between end plates 64.

Rods 66 further provide rotational limitation to housing 50. Arcuate portion 61 includes an opening 68 which forms a deposit opening in mail box 10 when shield 60 is affixed in the position shown in FIGS. 1 and 2.

Figure 9:
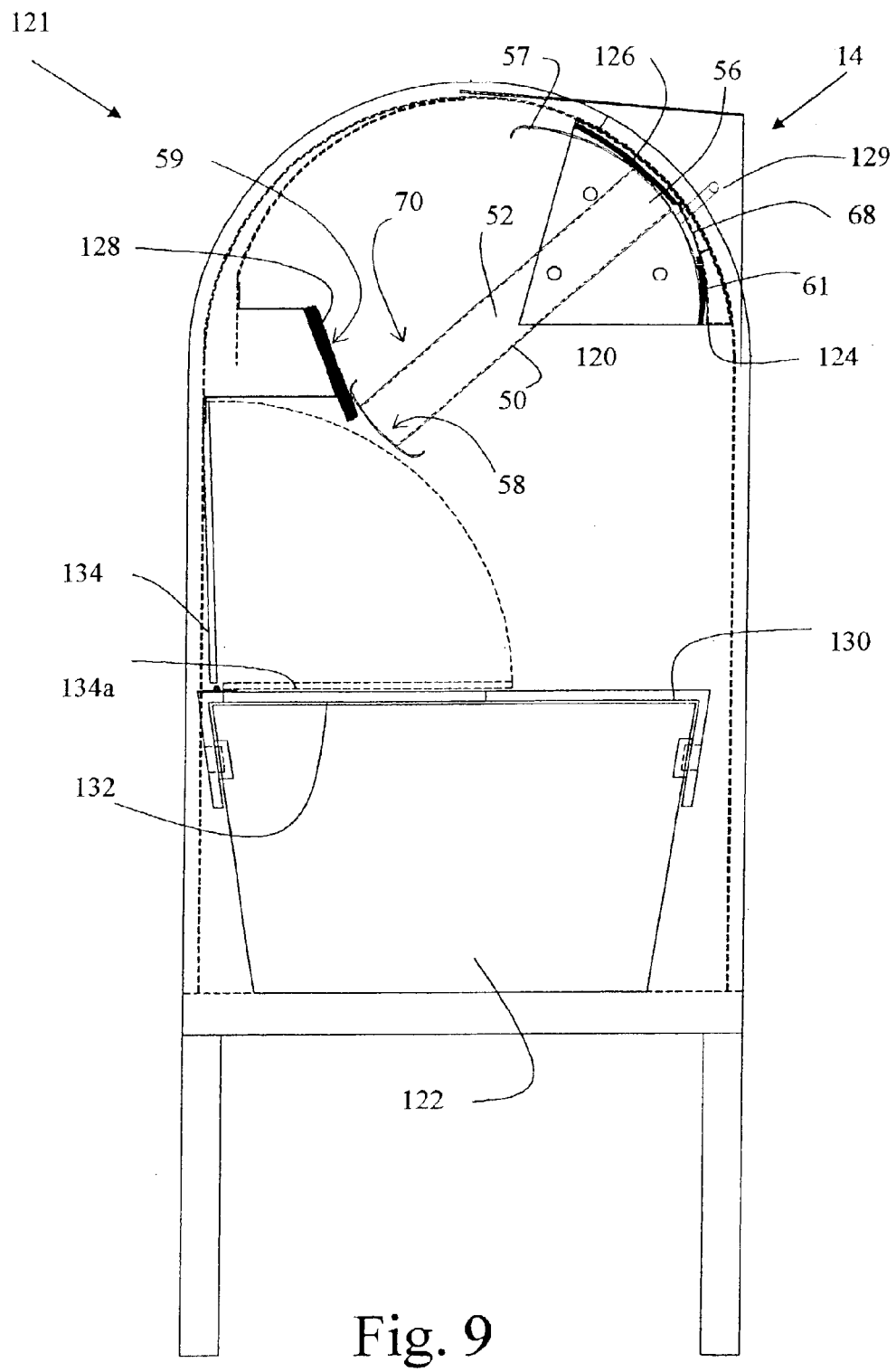
FIG. 9 is a side view diagram of the interior of a drop box constructed in accordance with another embodiment of the present invention.
Figure 10:
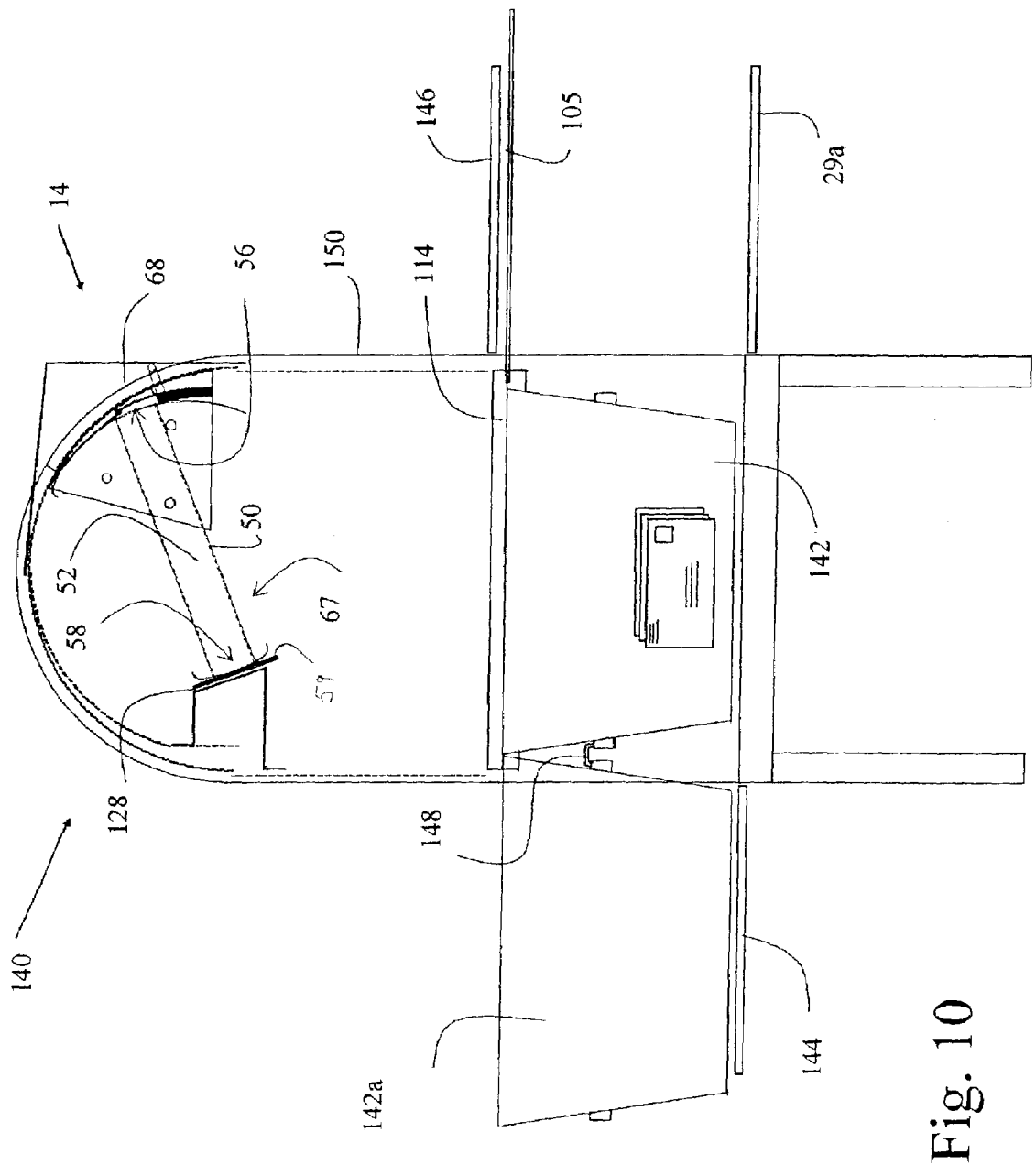
FIG. 10 is a side view diagram of the interior of a drop box constructed in accordance with yet another embodiment of the present invention.

When housing 50 and shield 60 are properly installed as shown in FIGS. 9 and 10, housing 50 is rotatable in one direction (clockwise) to a first position 67 (FIG. 10), to cause exposure of entrance 56 by alignment with mail box opening 68. Housing 50 is further rotatable in a second (counter-clockwise) direction to a second position 70 (FIG. 9), for causing the misalignment of entrance 56 with opening 68 and thereby the closure of entrance 56. Housing 50 is balanced to rest in position 70 (FIG. 9) when not in use, which further insures that any mail within chamber 52 passes through exit 58.

Mail box 10 further includes a closure surface 59 (FIG. 9) which is affixed to mail box 10 and located to cause closure of exit 58 when housing 50 is in the first rotational position 67 (FIG. 10) and entrance 56 is open. As shown in FIGS. 9 and 10, entrance 56 of reception chamber 52 is directed generally upwardly from chamber 52 and exit 58 is directed generally downwardly from chamber 52 to enable gravitational movement of items through chamber 52.

In this manner, housing 50 forms another embodiment of the present invention, namely a deposit port structure for a mailbox. Housing 50 forms a reception chamber 52 adapted for receiving items deposited into mail box 10, which housing 52 includes an entrance 56 to chamber 52 and is adapted to allow opening of entrance 56 for receiving deposited items in reception chamber 52. Deposit port 14 may also include a drop box opening 68 formed as part of securable enclosure 12, wherein housing 50 is rotatably mounted within drop box 10 for causing exposure of entrance 56 through drop box opening 68 by rotational alignment with drop box opening 68 and for causing closure of entrance 56 by rotational misalignment with drop box opening 68.

Housing 50 further includes an exit 58 from chamber 52 and is adapted to open exit 58 by rotation of housing 50 after closure of entrance 56. Closure surface 59 is affixed to mailbox 10 in a position to block exit 58 while entrance 56 is exposed through the mailbox opening 68. Also in this manner, housing 50 is rotatable between a first position of alignment between entrance 56 and opening 68 and a second position 70 wherein exit 58 is open. Housing 50 is further balanced to assume a rest position 70. Flange 57, which extends away from entrance 56 in both directions of rotation of housing 50, is adapted to isolate a user of drop box 10 from items previously passed through depository port 14.

Figure 5:
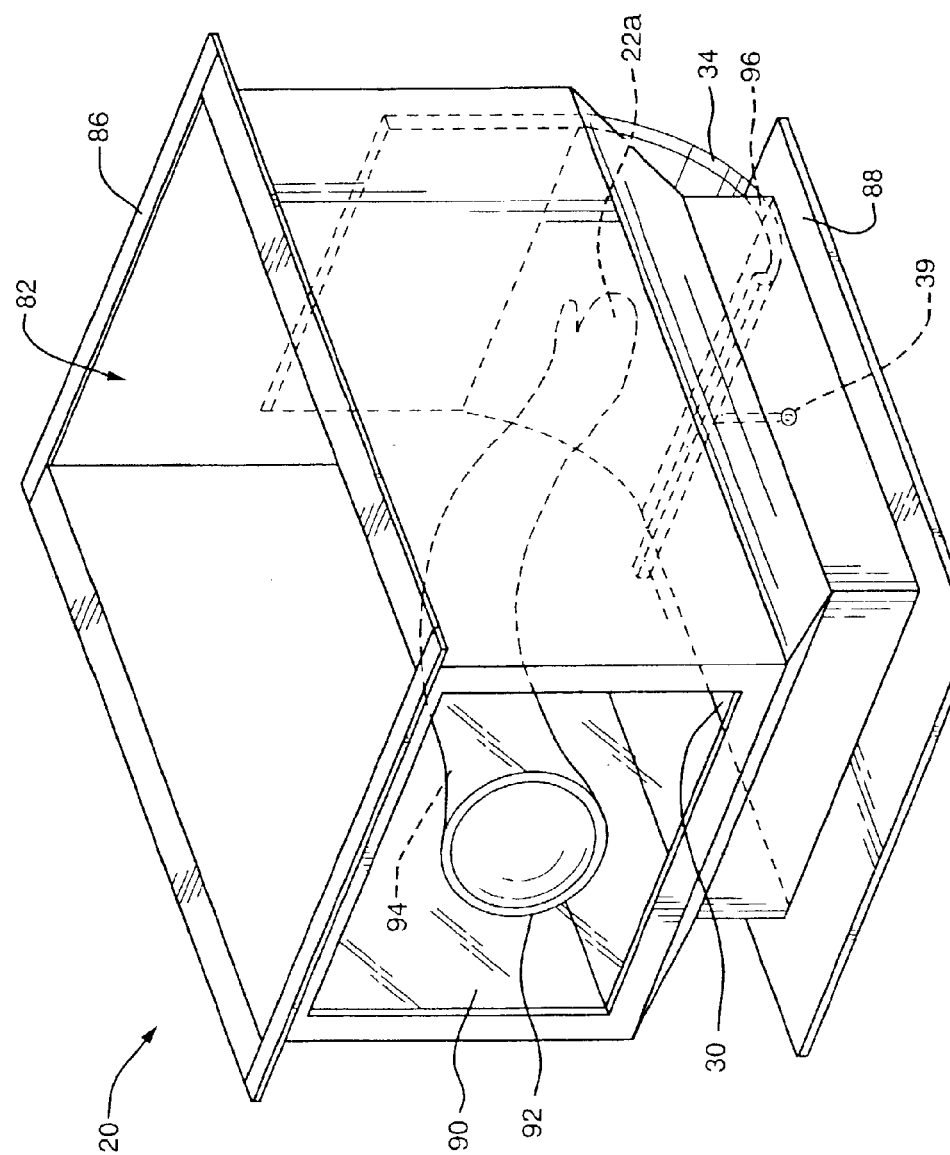
FIG. 5 is a perspective view of yet another portion of the drop box of FIGS. 1 and 2.

Duct 20 is shown in FIG. 5 in a form that may be retrofitted to a standard mailbox. Duct 20 is rectangular in shape and includes an upper opening 82 and a lower opening 30 as identified in FIG. 1. As mentioned, opening 30 defines a closeable opening for a mail container 18. It is desirable to restrict the opening of opening 30 to a size which is smaller than the dimensions of a container 18 so that deposited mail will all be directed into container 18 and not fall in between container 18 and the sides of mail box 10 (FIG. 2). Duct 20 further includes an upper flange 86 and a lower flange 88 which are affixed to mail box 10 to further define the securable enclosure of mail box 10. FIG. 5 also shows shutter 34 passing through an opening 96 in the side of duct 20 to partially close opening 30. Coupling 39 is used to connect shutter 34 to container 18 (FIG. 2).

One side of duct 20 is formed by a clear or transparent panel 90 that thereby creates a view port into the securable enclosure 12 and specifically provides visual access to opening 30. Transparent panel 90 may be made from a variety of durable plastic materials, such as Lexan®. Transparent panel 90 further includes an opening 92 formed therein for allowing a hazardous material glove or mitt 22a to be affixed thereto. The hazardous material mitt 22a includes an open end 94 which coincidences with and is sealed along opening 92 in transparent panel 90. This enables manual insertion into mitt 22a while isolating a user of mitt 22a from items located within the securable enclosure 12.

In this manner, a view port is provided in the form of transparent panel 90 located in a side of securable enclosure 12 and is adapted to allow viewing of the opening 30 within securable enclosure 12. A securable door 26 (FIGS. 1 and 2) is further provided to cover transparent panel 90. Manipulation device 22 may thus take the form of a hazardous material mitt 22a or glove (FIG. 2) extending into mail box 10 and having open end 94 for manual insertion, which open end 94 is sealed to a side of mail box 10 to isolate a user of mitt 22a or glove from items within mail box 10. Open end 94 may be sealed to transparent panel 90 that forms a view port into securable enclosure 12. Shutter 34 may be included and adapted for closing the opening 30, and duct 20 and a side of securable enclosure 12 may form a chamber adapted for storing shutter 34 in an open position.

Figure 6:
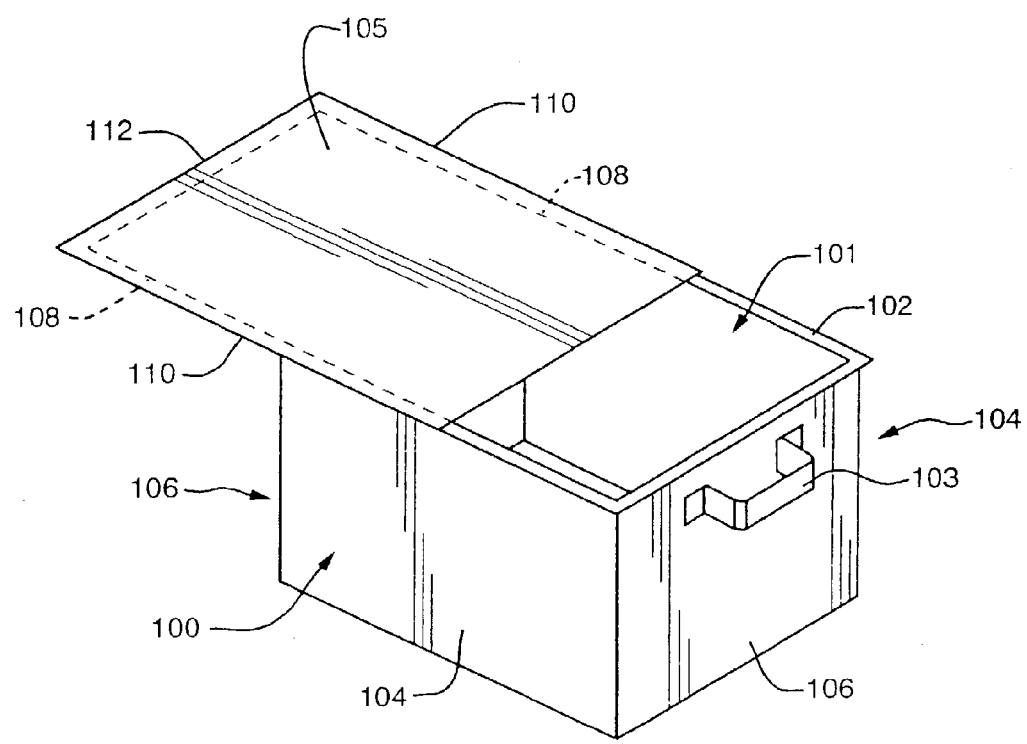
FIG. 6 is a perspective view of a receptacle for receiving deposited items in the drop box of FIGS. 1 and 2.

FIG. 6 is an isometric view of a closeable container 100 identical to container 18 of FIG. 2, being partially closed by a cover 105 (identical to cover 40 of FIG. 2). Container 100 is approximately the size of a standard mail flat tray and has an open top 101. Container 100 includes a handle 103 and a circumferential flange 102 which extends horizontally outwardly from open top 101 on both opposing sides 104 as well as ends 106 of container 100. Circumferential flange 102 is used for sealing cover 105 to container 100. Cover 105 includes a lip 108 (shown in phantom) along opposing sides 110 and one end 112. Lip 108 is adapted to engage flange 102 of container 100 in the manner shown.

Figure 7:
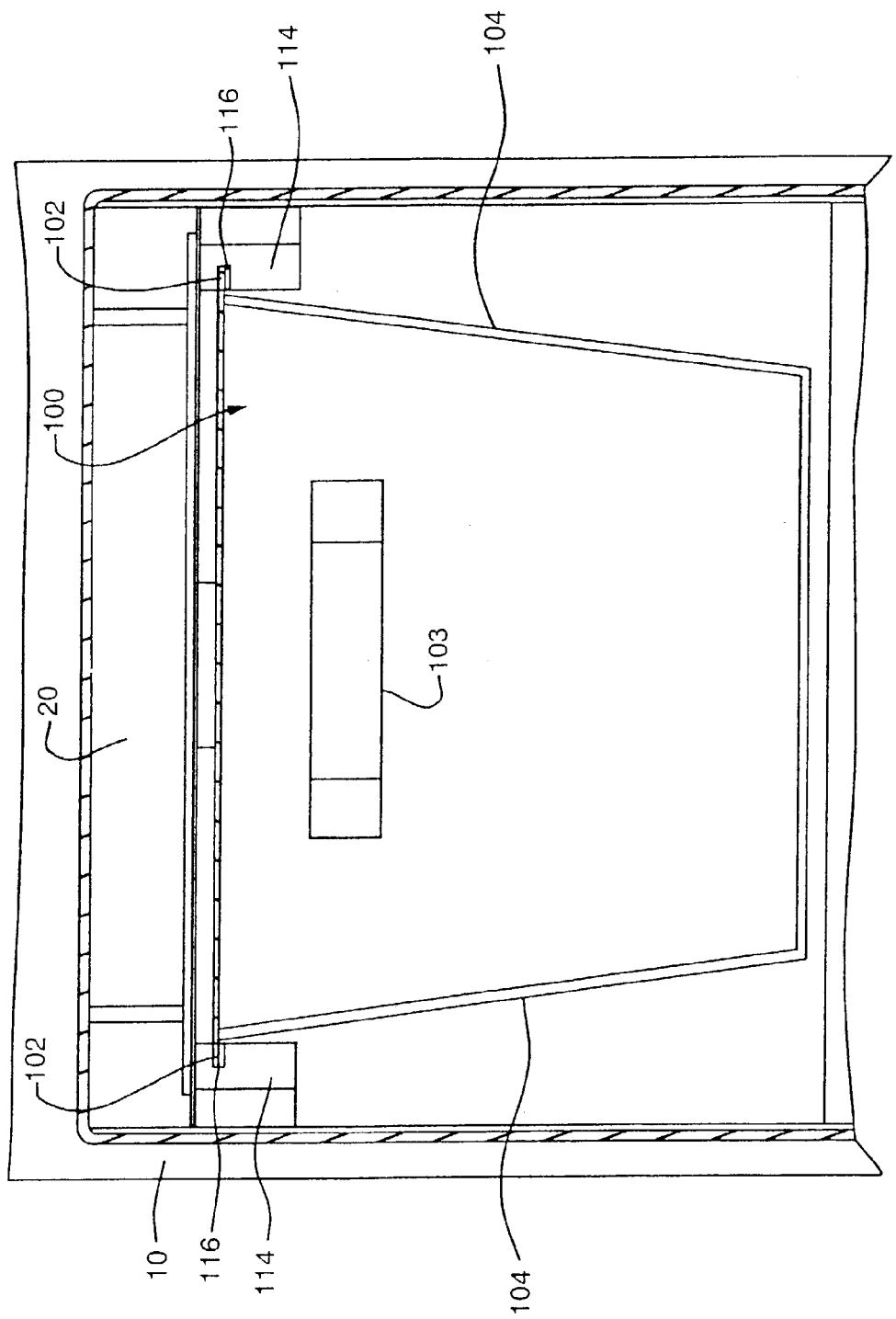
FIG. 7 is a different side view diagram of a portion of the interior of the drop box of FIGS. 1 and 2.
Figure 8:
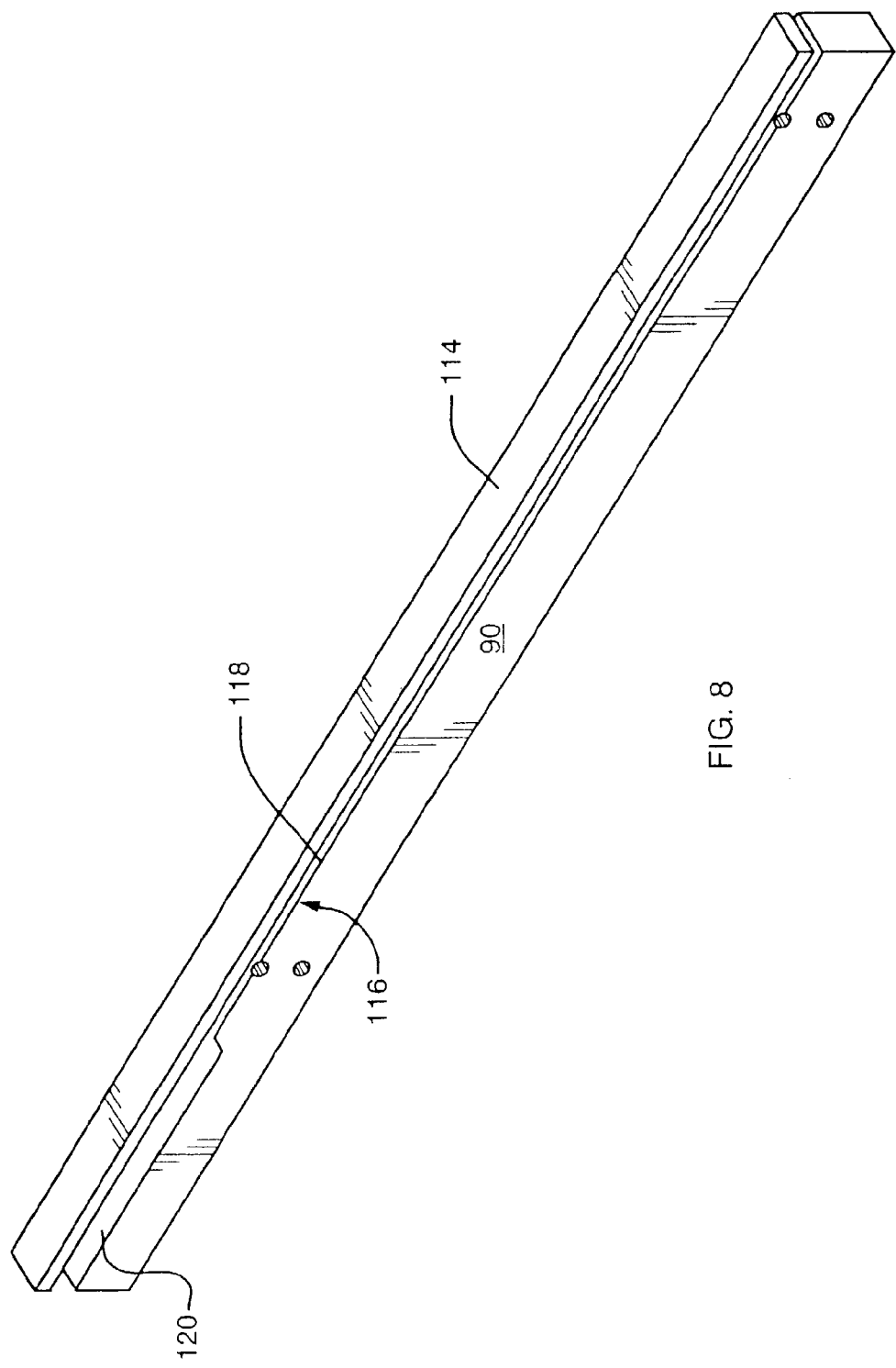
FIG. 8 is a perspective view of an internal element of the drop box of FIGS. 1 and 2.

FIG. 7 is a side view of a portion of the mail box 10 of FIG. 1, which portion includes the closeable container 100 without a cover. Flange 102 is engaged by a pair of guide rails 114. Guide rails 114 are affixed to mail box 10 to engage the flange 102 on opposing sides 104 of container 100 and to support container 100 in close proximity to duct 20. Guide rails 114 each include a slot 116 for accepting flange 102 (FIG. 6). A guide rail 114 is shown in greater detail in FIG. 8, with slot 116 including a narrower portion 118 and a wider portion 120. Narrow portion 118 is located within the main body of mailbox 10 (FIG. 2), and wider portion 120 is located in extension housing 29 (FIG. 2). In of this manner, wider portion 120 is adapted to handle both flange 102 and cover 105. In practice, cover 105 is located within wider portion 120 and container 18 is pulled from mail box 10 by handle 103 to maintain isolation of the contents of container 100 by closing container 100 with cover 105 as it is withdrawn from mail box 10.

In this manner, container 100 may be a standard size mail flat tray having a rectangular open top 101 or a hamper 214 (FIG.14) discussed below. A closure device in the form of cover 105 is thereby adapted to engage and close open top 101 during removal of container 100 from securable enclosure 12 and substantially prevent air from escaping from container 100. Also, a pair of opposed, substantially horizontal rails 114 are provided and adapted for engaging container 100 within securable enclosure 12. Guide rails 114 are further adapted to engage cover 105 during removal of container 100 from securable enclosure 12.

FIG. 9 is a schematic side view of another embodiment of the present invention generally including a mailbox 121, a deposit port 14 and a closeable container 122. The same reference numbers are used to identify elements that are substantially identical in previous drawings. Deposit port 14 is shown with chamber or housing 52 located in rest position 70. Deposit port 14 is shown in greater detail with a multiplicity of gaskets 124, 126, and 128. Gaskets 124 and 126 are compressible and located between flange 57 and arcuate portion 61 of shield 60. In one embodiment, gaskets 124, 126 and 128 are made from Neoprene® rubber, although any comparable material may be used. In this manner, airborne particulate contamination located within mailbox 121 is prevented from escaping through deposit port 14. Deposit port 14 is also shown to include a handle 129 for user operation.

Container 122 is shown to be generally rectangular and include a cover 130 for closing the top thereof. Cover 130 includes an opening 132 and a door 134 hinged to cover 130 and adapted to close opening 132. Mailbox 121 may further include a manipulation device (not shown) to allow closure of door 134 prior to removal of container 122 from mailbox 121.

FIG. 10 is schematic side view of a further embodiment of the present invention generally including a mailbox 140, a deposit port 14 and a closeable container 142. Housing 50 is shown to be located in a position of rotation 67 wherein entrance 56 is in alignment with opening 68 of shield 60, thereby allowing the deposit of items into the chamber 52 of housing 50. In an operative position, gasket 128 is shown to form closure surface 59 which contacts and blocks exit 58 of chamber 52.

In one embodiment, arcuate shield 61 has a radii of 7.875" and flange 57 has a radii of 7" leaving room for the gaskets or seals 124, 126. Axel 54 is 5" from shield 57, which makes flange 57 swing in an elliptical arc. Gaskets 124 and 126 are in a frictional state in the middle of the travel arc and in compression at each end 67, 70 of the travel arc.

Mailbox 140 includes a pair of securable doors 144, 29a that are located on opposing sides of mailbox 140 and oriented generally orthogonally to horizontal rails 114. Hinged door 144 provides an entrance into mailbox 140 for empty mail container 142a, while door 29a (similar to door 29 of FIGS. 1 and 2) provides an exit for removing full mail container 142.

FIG. 10 also shows the additional door 146 that may be hinged to open downwardly and expose a transparent panel 150 similar to panel 90 (FIG. 5). Hinged door 146 may also be used to support cover 105 during the extraction of mail container 142.

In a this manner, horizontal rails 114 and doors 144, 29a are adapted to allow simultaneous insertion of one container 142a into mail box 140 and removal of another container 142. Empty mail container 142a may also be coupled by a coupling 148 to a full container 142, and container 142 may be pulled from mailbox 140 resulting in the pulling of mail container 142a into mailbox 140. At the same time, a cover 105 may be positioned to engage and close container 142 as it is withdrawn from mailbox 140. Alternatively, empty container 142a may be used for pushing full container 142.

Figure 11:
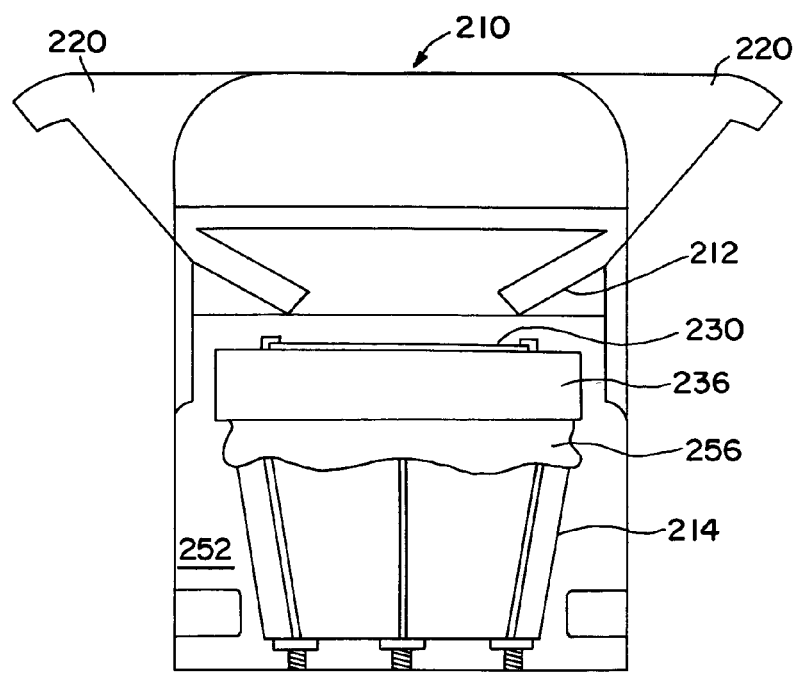
FIG. 11 is a sectional view of one embodiment of the collection box of the present invention.
Figure 12:
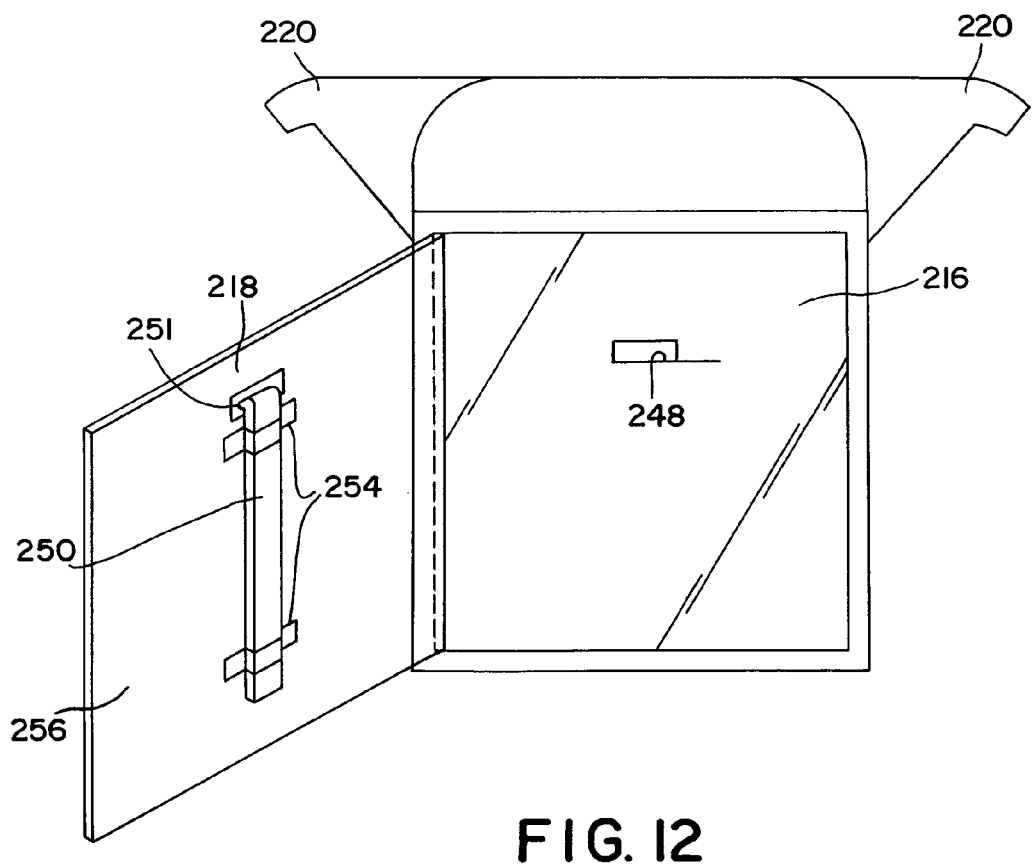
FIG. 12 is a side view of the collection box of FIG. 11 showing the interior access door having an access port in its closed position with the exterior sealed access door opened.

FIGS. 11 and 12, show a conventional jumbo collection box 210 which is adapted with an improved mail chute 212, a sealable hamper 214, and an interior access door 216 and an exterior sealed access door 218. Mail articles are deposited into a mail slot 220 that guides the mail article into the mail chute 212 and into the awaiting sealable hamper 214.

Figure 13:
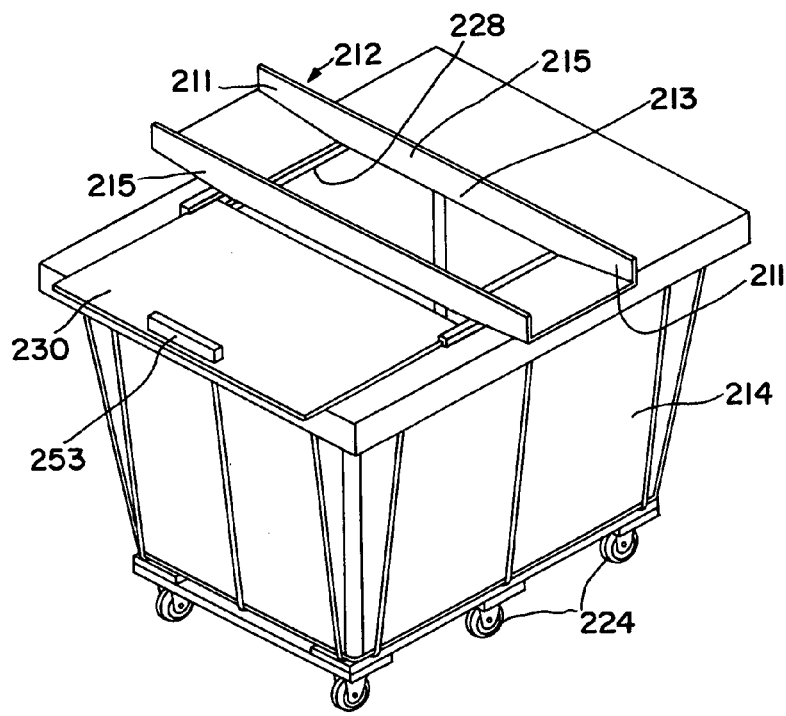
FIG. 13 is an isometric view of the chute disposed above the hamper of the collection box of FIG. 11.

The mail chute 212 is shown in FIG. 13 as having a generally horizontal central section 213 with the ends inclined upwardly so that the mail coming down the mail slot 220 is directed into the hamper opening 228. The chute may have vertical flanges 215 to assist in properly guiding the mail.

Now turning to FIG. 13, mail chute 212 is illustrated disposed above the sealable hamper 214. The mail chute 212 feeds mail articles from either side of the collection box 210 through dual inlets 211 for increased throughput.

Figure 14:
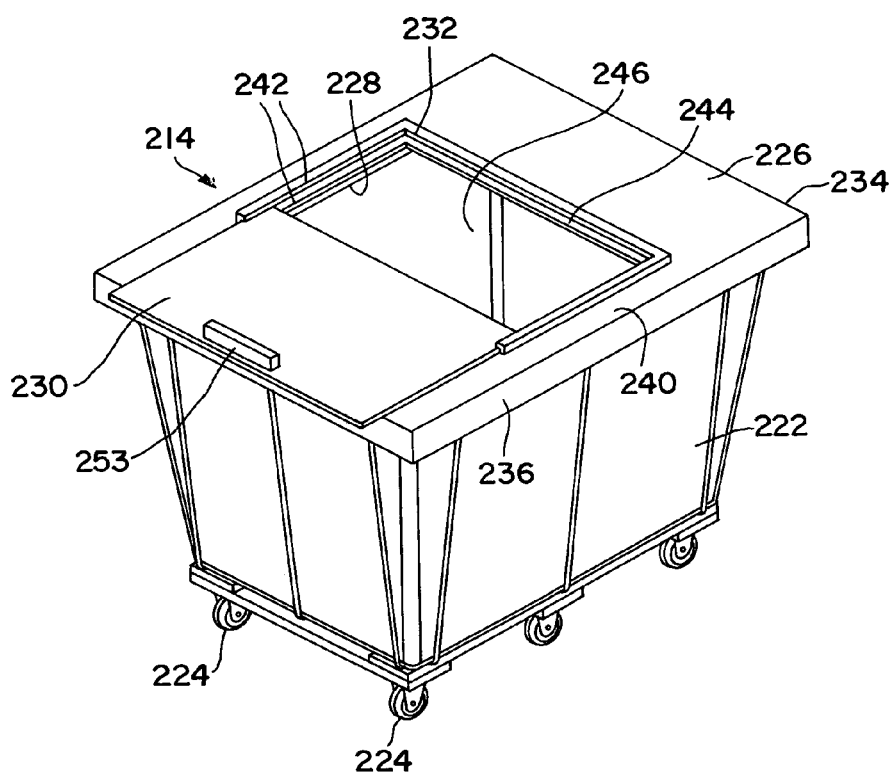
FIG. 14 is an isometric view of the hamper of FIG. 13 with the slidable door open illustrating one embodiment of the sliding door mechanism.
Figure 15:
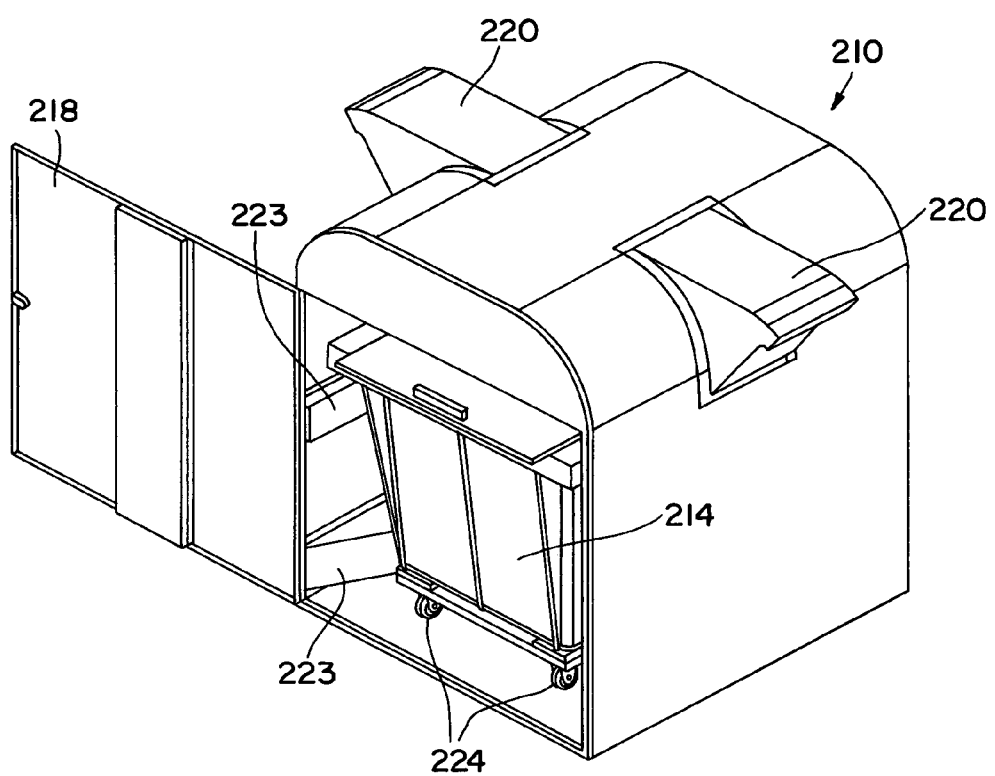
FIG. 15 is an isometric view of the jumbo collection box with the exterior door open and the interior door not shown (for purposes of clarity).

Now referring to FIG. 14, one embodiment of the sealable hamper 214 includes a conventional hamper 222, preferably made of canvas, wheels 224, lid 226 with a mail entry hole 228, sliding door 230 and sliding door mechanism 232. The lid 226 can be made of plywood, plastic, metal or any suitable material. The perimeter 234 of the lid 226 is fitted with a form skirt 236 to seal the rim (not shown) of the sealable hamper 214. The weight of the lid 226 and the skirt 236 assures that lid 226 conforms to the possible unevenness of the wire frame rim 238.

Further, the lid 226 includes a hole 228, preferably near its center portion 240, for the mail articles to enter the sealable hamper. The hole 228 is covered when the hamper 214 is transported to a distribution center by a cover or door 230. The door 230 is in slidably contact with respect to the lid 226 by a sliding door mechanism 232. One embodiment of the sliding door mechanism 230 includes two opposing tracks 242 disposed on either side of the hole 228 and preferably of length greater that the hole 228. A sealing strip 244 is disposed perpendicular to and abutting the tracks 242. The door 230 can be in frictional contact with the tracks 242 and lid 226, thereby creating a seal substantially no air leakage from the interior 246 of the sealable hamper 214 to the outside environment. Alternatively, sealing material (not shown), such as foam, can be adapted to the lid 226 and/or tracks 242 such that the door 230 can be in slidable contact with the foam and the interior 246 of the hamper 214 is isolated from the outside atmosphere.

Now returning to FIG. 12, the collection box 210 includes two access doors. The exterior access door 218 is similar to conventional jumbo collection box access doors with an improved seal to create a substantially air tight seal. The interior access door 216 is transparent such that the sealable hamper 214 and the slidable door 230 are visible. The interior access door 216 includes an access port 248 sized for insertion of a tool 250 or hand to open and close the slidable door 230. The tool 250 is sufficiently long, such as a rod with a hook end 251, to enter the interior 252 of the collection box 210 is actuate the door 230 open and closed by pushing or pulling on a door handle 253 or the like. One potential storage location for the tool 250 is on brackets 254 or the like on the interior side 256 of the exterior access door 218.

Now returning to FIG. 11, an impervious liner 256, preferably made of polymers, can be added to increase containment collection. The impervious liner 256 can be a rigid molded structure or a flexible bag.

In operation, the carrier unlocks the exterior access door 218 of the collection box 210 and views the interior 252 of the collection box 210 for mail overflow or jams. The carrier removes the tool 250 from its storage place, inserts the tool 250 into the port 248, contacts door handle 253, and slides the door 230 closed. The carrier unlocks the interior access door 216 and slides the sealed hamper 214 out of the collection box 210 for transportation. A replacement hamper 214 pre-fitted with a lid 226 is pushed in and located inside the collection box 210. The collection box 210 has guides 223 for properly guiding the hamper 214 into its proper location in the collection box 210. The carrier opens the sliding door 230 with the tool 250 by hooking handle 253 with the hook end 251 of the tool 250, thereby exposing mail entry hole 228 and allowing for acceptance of mail articles into hamper 214. The carrier closes and locks the access doors 216, 218 and transports the removed hamper 214 to a distribution facility.

It will now be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

What is claimed is:

1. A mail drop box for isolating mail deposited therein, comprising:
   a. a drop box housing;
   b. a closable, removable chamber inside said drop box housing for receiving mail, said chamber being defined by a removable container having an opening in the top;
   c. a plurality of mail transmitting chutes each having a deposit port at its upper end and an exit port at its lower end and arranged to receive mail through the deposit port and direct such mail into the closable chamber;
   d. means for closing the opening in the removable container when desired to isolate the mail therein from the ambient atmosphere and permit removal of the container without exposing the ambient atmosphere to any hazardous material particles which may be on or in such mail;
   e. a removal door in said drop box housing to permit removal of said removable container therethrough; and
   f. a transparent door located adjacent to but inside of said removal door for allowing viewing of said opening of said removable container within said drop box housing when said removal door is open.

2. A drop box as defined in claim 1 wherein said transparent door includes a manipulation access port;
   a manipulation device capable of extension into said drop box housing through said manipulation access port to manipulate said closing means by a user located outside said drop box housing without exposing the user to any hazardous materials which may be contained in or on the mail located within said removable container.

3. A drop box as defined in claim 2 wherein said manipulation device is an elongated member capable of extending into said drop box housing to actuate said closing means.

4. A drop box as defined in claim 2 wherein said removable container is a mail flat tray having a rectangular open top defining said opening and said closing means including a top cover adapted for engaging said opening in the top of the container and preventing air from escaping from said container.

5. A drop box as defined in claim 2 wherein said closing means closes said opening of said container during removal of said container from said drop box housing.

6. A drop box as defined in claim 5 wherein said closing means is a cover to engage and to close said container during removal of said container from said drop box housing.

7. A drop box as defined in claim 6 further comprising a pair of opposed horizontal rails for engaging said container within said drop box housing and for engaging said cover during removal of said container from said drop box housing.

8. A drop box as defined in claim 7 further comprising third and fourth securable doors located in opposing sides of said drop box housing and oriented generally orthogonally to said horizontal rails, wherein said horizontal rails and said third and fourth doors allow insertion of one removable container into said drop box housing and removal of another removable container from said drop box housing simultaneously.

9. A drop box as defined in claim 2 wherein said removable container is mounted on wheels for easy removal.

10. A mail drop box for isolating mail deposited therein comprising:
    a. a drop box housing;
    b. a closable, removable chamber inside said drop box housing for receiving mail, said chamber being defined by a removable container having an opening in the top;
    c. a plurality of mail transmitting chutes each having a deposit port at its upper end and an exit port at its lower end and arranged to receive mail through the deposit port and direct such mail into the closable chamber;
    d. means for closing the opening in the removable container when desired to isolate the mail therein from the ambient atmosphere and permit removal of the container without exposing the ambient atmosphere to any hazardous material particles which may be on or in such mail;
    said closing means including a door hinged to the top of said removable container and arranged to be left open for receiving mail and for closure prior to removal of said container from said drop box housing.

11. A mail drop box for isolating mail deposited therein, comprising:
    a. a drop box housing;
    b. a closable, removable chamber inside said drop box housing for receiving mail, said chamber being defined by a removable container having an opening in the top;
    c. a plurality of mail transmitting chutes each having a deposit port at its upper end and an exit port at its lower end and arranged to receive mail through the deposit port and direct such mail into the closable chamber;
    d. means for closing the opening in the removable container when desired to isolate the mail therein from the ambient atmosphere and permit removal of the container without exposing the ambient atmosphere to any hazardous material particles which may be on or in such mail, said closing means being a shutter mounted to said removable container; and
       wherein said chute and a side of said drop box housing form a compartment for storing said shutter in an open position, and said shutter is arranged for removable coupling to said container to provide closure of said shutter with the removal of said container from said drop box housing.

12. A mail drop box adapted for isolating items deposited therein, comprising:
    a securable enclosure;
    a depository port forming part of said securable enclosure and adapted to allow items to be dropped through said depository port into said securable enclosure;
    a closeable container having an opening and located within said securable enclosure for receiving items dropped into said securable enclosure; and
    a closure device on said container for closing said opening of said container;
    a duct forming a channel for directing items from said depository port to said opening of said container when items placed in said depository port are to be directed into said container, and a device for preventing items from being directed through said channel when items placed in said depository port are not to be directed into said container.

13. A drop box as defined in claim 12 wherein said device may be used to prevent items from being directed into said container prior to removal of said container.

14. A drop box as defined in claim 12 wherein said device may be used to prevent items from being directed into said container during removal of said container.

15. A drop box adapted for isolating items deposited therein, comprising:
   a securable enclosure;
   a depository port forming part of said securable enclosure and adapted to allow items to be dropped through said depository port into said securable enclosure;
   a closeable container having an opening and located within said securable enclosure for receiving items dropped into said securable enclosure; and
   a closure device on said container for closing said opening of said container,
   said depository port including a housing forming a reception chamber adapted for receiving items deposited into said drop box, and further wherein said housing includes an entrance and is adapted to allow opening of said entrance for receiving deposited items in said reception chamber; and further including a duct for directing items from the depository port to the opening in said container when deposited items are to be conducted to the container, and a device for preventing the directing of items from the depository port to the opening in said container when the container is to be removed.

16. A drop box adapted for isolating items deposited therein, comprising:
   a securable enclosure;
   a depository port forming part of said securable enclosure and adapted to allow items to be dropped through said depository port into said securable enclosure;
   a closeable container having an opening and located within said securable enclosure for receiving items dropped into said securable enclosure;
   a closure device on said container for closing said opening of said container; and
   a chute in said enclosure forming a channel for directing items from said depository port to said opening of said container when items placed in said depository port are to be directed into said container, and a device in said enclosure for preventing items from being directed through said channel when items placed in said depository port are not to be directed into said container.

17. A drop box adapted for isolating items deposited therein, comprising:
   a securable enclosure;
   a depository port forming part of said securable enclosure adapted to allow items to be dropped through said depository port into said securable enclosure;
   a closeable container having an opening and located within said securable enclosure for receiving items dropped into said securable enclosure;
   a closure device on said container for closing said opening of said container; and
   said depository port includes a housing forming a reception chamber adapted for receiving items deposited into said drop box, and further wherein said housing includes an entrance and is adapted to allow opening of said entrance for receiving deposited items in said reception chamber; and further including a chute for directing items from the depository port to the opening in said container when deposited items are to be conducted to the container, and a device for preventing the directing of items from the depository port to the opening in said container when the container is to be removed.

18. A drop box as defined in claim 17 wherein said chute forms a channel for directing items which it receives into said container when desired.

* * * * *